(12) United States Patent
Makino

(10) Patent No.: US 6,306,201 B1
(45) Date of Patent: Oct. 23, 2001

(54) BIVALENT IRON COMPOUNDS

(75) Inventor: Shinzi Makino, Aichi-ken (JP)

(73) Assignee: I.B.E. Company, Ltd., Aichi-ken (JP)

( * ) Notice: Subject to any disclaimer, the term of this patent is extended or adjusted under 35 U.S.C. 154(b) by 0 days.

(21) Appl. No.: 09/326,967

(22) Filed: Jun. 7, 1999

Related U.S. Application Data

(63) Continuation of application No. 08/822,557, filed on Mar. 19, 1997, now abandoned, which is a continuation of application No. 08/674,467, filed on Jul. 2, 1996, now abandoned, which is a continuation of application No. 08/367,761, filed on Jan. 3, 1995, now abandoned, which is a continuation of application No. 07/828,883, filed on Jan. 29, 1992, now abandoned.

(51) Int. Cl.$^7$ .................................................. C01G 49/00

(52) U.S. Cl. .................................. 106/14.13; 106/14.15; 106/14.12; 106/14.18; 106/18.32; 106/15.05; 424/70.1; 424/648; 252/389.53; 252/394; 252/400.53; 252/392; 252/405; 252/403; 252/401; 252/370; 510/119; 510/130; 510/401; 510/402; 510/479

(58) Field of Search ................................... 424/70.1, 648; 510/119, 130, 401, 402, 479; 106/14.13, 14.15, 14.42, 14.18, 18.32, 15.05; 252/387.53, 394, 400.53, 392, 4.55, 403, 401, 370

(56) References Cited

FOREIGN PATENT DOCUMENTS 2-142760 * 5/1990 (JP) .

* cited by examiner

*Primary Examiner*—C. Melissa Koslow
(74) *Attorney, Agent, or Firm*—Foley & Lardner

(57) ABSTRACT

This invention relates to a bivalent iron compound comprising a bivalent iron salt, an amino acid and a reducing material. It is known that bivalent iron salts exhibit specific effects in wide applications, for example, agricultural applications such as modification of soil quality, fishing applications such as quality preservation of fishes, medical applications such as treatment of diseases and industrial applications such as prevention of metal corrosion and purification of waste water and exhaust gas. However, the conventional bivalent iron salts suffer a problem that they cannot exhibit such effect for extended periods. This invention was successful in chemically stabilizing the bivalent iron salts by adding amino acids and reducing materials so as to sustain the effects inherent in the bivalent iron salts and to enable utilization thereof in industrial applications.

22 Claims, No Drawings

2

BIVALENT IRON COMPOUNDS

This is a continuation of application Ser. No. 08/822,557, filed Mar. 19, 1997, now abandoned, which is a continuation of application Ser. No. 08/674,467, filed Jul. 2, 1996, now abandoned, which is a continuation of application Ser. No. 08/367,761, filed Jan. 3, 1995, now abandoned, which is a continuation of application Ser. No. 07/828,883, filed Jan. 29, 1992, now abandoned, which was the National Stage of International Application No. PCT/JP90/00651, filed Nov. 24, 1988.

FIELD OF THE TECHNOLOGY

This invention relates to a bivalent iron compound which can be utilized widely in various applications such as for healthy growth of animals and plants, promotion of biological activities, treatment of diseases, quality preservation of foods, prevention of perishing, prevention of molding, prevention of corrosion and modification or purification of water and air.

TECHNICAL BACKGROUND

As disclosed in Japanese Provisional Patent Publication No. 190226/1984, when a bivalent or tervalent iron salt to be obtained by introducing a tervalent iron salt to a large amount of strongly alkaline aqueous solution or by introducing a bivalent iron salt into a large amount of strongly acidic aqueous solution is dissolved in water, it converts the water to a specific nonionic reaction system. It is also known that such salt inhibits various ionic reactions which occur in ordinary water systems and exhibits specific and even miraculous actions and effects against the objects to be treated. In other words, it is known that such iron salts exhibit antiseptic actions, metal corrosion inhibitory actions and soil trouble removing actions as well as physiological actions such as antivirus actions, antitumor actions and immunological actions.

It is true that the bivalent or tervalent iron salts have excellent properties as described above. However, the bivalent iron salts suffer a problem that they are particularly susceptible to oxidation and cannot maintain their original excellent properties since their effects are halved after one month from production, which has been a serious problem in practical applications.

Therefore, it is an object of this invention to provide a bivalent iron compound that overcomes the above problem and is capable of exhibiting the excellent properties as described above over a long time.

DISCLOSURE OF THE INVENTION

In order to solve the above problem, this invention provides a bivalent iron compound containing a bivalent iron salt, an amino acid and a reducing material.

When the present bivalent iron compound is applied to animals or plants, their biological activities and growth are promoted. When the bivalent iron compound is applied to foods, it can prevent them from perishing and maintain their freshness for a long time. It also shows therapeutic actions against diseases. Besides, the bivalent iron compound has an action of modifying or purifying soil, water and air, an antistatic action, a frictional resistance reducing action, a concrete reinforcing action, a snow melting action, etc.

The bivalent iron compound can be converted into a chemically stable substance by adding an amino acid thereto. Further, oxidation of the bivalent iron salt can be prevented considerably by the addition of a reducing material. The various actions inherent in the bivalent iron salt as described above can be maintained for a long time by the synergistic effect to be brought about by the combination of the reducing material and amino acid.

It is preferred to dissolve the bivalent iron salt in water to provide an aqueous solution. When the bivalent iron compound is dissolved in water, the actions of the bivalent iron salt can effectively be exhibited. It is not known why the aqueous bivalent iron salt solution can exhibit such actions effectively. However, it can be considered that the aqueous solution inhibits various ionic reactions which occur in ordinary water systems and exhibits a specific action of converting the water systems into nonionic reaction systems.

Further, it is preferred to treat inorganic materials with the aqueous bivalent iron salt solution by dipping. When an inorganic material is dip-treated in the aqueous bivalent iron salt solution, the bivalent iron compound can be carried stably by the inorganic material. The thus treated inorganic material exhibits a water purifying action, an air purifying action and a gasoline modifying action.

Next, typical examples of each material will be described. The bivalent iron salt includes inorganic salts such as iron dichloride ($FeC_2$), iron sulfate ($FeSO_4$), iron dinitrate ($Fe(NO_3)_2$) and triiron diphosphate ($Fe_3(PO_4)_2$), and organic acid salts such as iron diformate ($Fe(HCOO)_2$), iron diacetate ($Fe(CHCOO)$), iron dipropionate ($Fe(CH_3CHOO)_2$), iron oxalate ($FeC_2O_4$), iron tartrate ($FeC_4H_4O_6$) iron fumarate ($FeC_4H_2O_4$) and iron dilactate ($Fe(CH_3CHOHCOO)_2$).

In addition to the above, a reaction mixture of a tervalent iron salt and a reducing material to be described later can be used as the bivalent iron salt. The tervalent iron salt includes inorganic salts such as iron trichloride ($FeCl_3$), diiron trisulfate ($Fe_2(SO_4)_3$), iron trinitrate ($Fe(NO_3)_3$), iron phosphate ($FePO_4$), diiron diammonium tetrasulfate ($Fe_2(NH_4)_2(SO_4)_4$), and organic acid salts such as iron triformate ($Fe(HCOO)_3$), iron triacetate ($Fe(CH_3COO)_3$), iron citrate ($FeC_6H_5O_7$) and iron tristearate ($Fe(C_{17}H_{35}COO)_3$).

The amino acid includes monoamino-monocarboxylic acids such as glycine, alanine, leucine, tyrosine, threonine, serine, proline tryptophan, methionine, cystine and cysteine; monoamino-dicarboxylic acids such as asparagic acid and glutamic acid; and diamino-monocarboxylic acids such as lysine, arginine and histidine. It should be noted, however, that the amino acid is preferably added in an amount sufficient to react with the bivalent iron salt to form an organic complex and the like.

The reducing material includes aldehydes such as formaldehyde, acetaldehyde, formic acid and benzaldehyde; saccharides (sugars) such as cane sugar (sucrose), glucose and lactose; ascorbic acid, α-tocopherol; and metals such as iron, zinc and copper. The reducing material is preferably added in an amount sufficient to retain the bivalent iron salt in the bivalent form or to reduce the tervalent iron salt to a bivalent salt.

The inorganic material includes metals such as iron, zinc and copper, ceramics and inorganic salts. The ceramics include zeolite, alumina, silicon carbide, silicon nitride and cordierite.

PREFERRED EMBODIMENT OF THE INVENTION

Now typical embodiments of this invention will be described by way of Preparation Examples 1 to 3 in which bivalent iron salt solutions are prepared and Examples 1 to 41 in which the solutions are applied in various applications.

First, Preparation Examples 1 to 3 will be described.

PREPARATION EXAMPLE 1

To 1 liter of water were added 1 mole of iron sulfate hydrate, 0.1 to 3.0 moles of asparagic acid and 0.1 to 3.0 moles of sucrose, and the resulting mixture was stirred at 60° C. for 3 hours to give a dark brown aqueous solution.

PREPARATION EXAMPLE 2

To 1 liter of water were added 1 mole of iron trichloride hydrate, 0.1 to 3.0 moles of glycine and 0.1 to 3.0 moles of lactose, and the resulting mixture was stirred at 60° C. for 3 hours to give a dark brown aqueous solution.

PREPARATION EXAMPLE 3

To 1 liter of water were added 1 mole of iron trichloride hydrate, 0.1 to 3.0 moles of glutamic acid and 0.1 to 3.0 moles of glucose, and the resulting mixture was stirred at 60° C. for 3 hours to give a dark brown aqueous solution.

The aqueous bivalent iron salt solutions prepared in Preparation Examples 1 to 3 all retained the specific actions and effects characteristic to the aqueous bivalent iron salt solution, which will be described later, even after 6 months from preparation. This is considered to be attributable to the synergistic effect to be brought about by the combination of the amino acids, which chemically stabilize the salts in the form of organic complex, and the reducing material which considerably prevents oxidation of the bivalent iron salts. Such synergistic effect can be proved by the fact that the actions and effects of the bivalent iron salt cannot be maintained for a long time if either the amino acid or the reducing material is omitted.

Next, Examples 1 to 41 in which the aqueous bivalent iron salt solutions prepared above are applied in various applications will be described.

It should be noted that the aqueous bivalent iron salt solutions prepared in Preparation Examples 1 to 3 were diluted to appropriate molar concentrations when they are used in the respective examples. However, the concentration of the aqueous bivalent iron salt solution is not limited to the one shown in each example and can effectively be varied so long as the molar concentration of iron content is within the range of $10^{-6}$ to $10^{-21}$ moles/liter).

EXAMPLE 1

Promotion of biological activities of seed

Paddy rice seeds were immersed in the aqueous bivalent iron salt solution (iron content: $10^{-5}$ moles/liter) prepared in Preparation Example 1 for about 24 hours and then seeded. When yield of rice at cropping was determined for the area where the treated rice seeds were seeded (treated area) and for the area where untreated ordinary rice seeds were seeded (control area). The yield in the treated area was 12 hyo (hyo is a unit showing the yield of rice and corresponds to about 60 kilograms) per 10 acre, whereas that in the control area was merely 8 hyo. Thus, increase in the yield in the treated area was demonstrated.

On the other hand, the yield of rice when treated with the aqueous bivalent iron salt solution prepared in Preparation Example 2 and the same when treated with the aqueous bivalent iron salt solution prepared in Preparation Example 3 were 10.3 hyo and 8.5 hyo, respectively. The higher the concentration of the aqueous bivalent iron salt solution is, the higher the rice yield tends to be.

EXAMPLE 2

Modification of soil (1)

A 500 m² area soil was covered uniformly with 20 liters of the aqueous bivalent iron salt solution (iron content: $10^{-12}$ moles/liter) prepared in Preparation Example 1, and the treated soil was left to stand for 2 months. When the phosphate absorption coefficient was determined for the treated area and the untreated control area after 2 months from treatment, the treated area showed a value of 620 while the untreated control area showed a value of 930. Thus, modification of the treated soil was demonstrated.

It should be noted, however, that the aqueous bivalent iron salt solution can be applied so long as the molar concentration of iron is within the range of $10^{-6}$ to $10^{-21}$ moles/liter, preferably in the range of $10^{-12}$ to $10^{-15}$ moles/liter.

EXAMPLE 3

Modification of soil (2)

After a mixture of tuff loam, zeolite and molasses (100:100:1) was impregnated with the aqueous bivalent iron salt solution (iron content: $10^{-12}$ moles/liter) prepared in Preparation Example 1 at normal temperature for 24 hours, it was dried by exposure to sunlight. A 10 acre paddy field was covered with 60 kilograms of the thus treated soil mixture, and after plowing paddy rice plants were planted and left to stand for 5 months. When the phosphate absorption coefficient was determined for the treated area and the untreated control area after 5 months from treatment, the treated area showed a value of 608, while the untreated control area showed a value of 985. Thus, modification of the soil by covering with the soil mixture was demonstrated.

On the other hand, the yield of unmilled rice in the treated area and that in the control area were 522 kilograms and 360 kilograms, respectively. Thus, a 45% gain in the yield was demonstrated in the treated area. Incidentally, the mixing ratio of tuff loam:zeolite:molasses is not limited to the value specified above.

EXAMPLE 4

Reversing field depletion due to repetitive cropping

A potato field suffering from SOUKA BYO (a depletion in field productivity) caused by repeatedly planting the same crops, was covered with the soil mixture prepared in Example 3 in an amount of 60 kilograms per 10 ares of soil. When potatoes were planted in the thus treated field after plowing, no productivity depletion occurred before harvesting.

When a spinach field was treated in the same manner as described above, the depletion due to repetitive planting was cleared, and no depletion including depauperation occurred even after 20 repeated plantings.

EXAMPLE 5

Improvement of rooting rate

The roots of trees (50 Myrica rubra trees) were immersed in the aqueous bivalent iron salt solution (iron content: $10^{-15}$ moles/liter) prepared in Preparation Example 1 for about 24 hours before they were transplanted. When the rooting rate of the trees (the rate that the trees root in the ground) was determined for the thus treated trees and untreated trees, it was found that the rooting rate of the treated trees was 100% while that of the untreated trees was 85%. The effect of the present solution can be exhibited by immersion for a wide time range of 1 to 30 hours.

EXAMPLE 6

Quality preservation of fish (1)

Freshly caught tunas were immersed in the aqueous bivalent iron salt solution (iron content: $10^{-15}$ moles/liter) prepared in Preparation Example 1 and stored at 0° C. for 20 days. The thus treated tunas still retained their fresh colors in the gills and body even after 20 days. However, those tunas which were maintained immersed in an ordinary water showed discoloration in their gills and deterioration in the meat quality after 20 days. When these qualities were evaluated by means of K value (a chemical method of determining freshness), the treated tunas had a K value of 23, while the untreated tunas (treated with the ordinary water) had a K value of 64.

EXAMPLE 7
Quality preservation of fish (2)

Fresh crabs of the family Atelecyclidae were immersed in the aqueous bivalent iron salt solution (iron content: $10^{-15}$ moles/liter) prepared in Preparation Example 1 for 10 minutes and they were stored in a refrigerator (7° C.) for one month.

The thus treated crabs still retained their freshness with no smell even after storage for one month. However, the untreated crabs developed a putrid smell after storage for 1 month.

Furthermore, when oysters were tested in the same manner as described above, a similar effect was exhibited.

EXAMPLE 8
Cultivation of fish (1)

To a 1 ton aquarium were added the aqueous bivalent iron salt solution (iron content: $10^{-15}$ moles/liter) prepared in Preparation Example 1 and NaCl in such amounts that the resulting solution had a salt concentration corresponding to that of sea water. Thereafter, 200 horse mackerels were introduced and bred therein for 7 days. None of the fish bred in this aquarium died, but in an aquarium charged with an ordinary saline solution having the same salt concentration as the sea water, 30 out of 200 fish died.

EXAMPLE 9
Cultivation of fish (2)

To a 1 ton aquarium were charged the aqueous bivalent iron salt solution (iron content: $10^{-15}$ moles/liter) prepared in Preparation Example 1 together with a sea water, and 150 scallops were introduced and bred therein for 15 days. None of the scallops bred in this aquarium died, but in an aquarium charged with an ordinary sea water, 42% of the scallops died.

EXAMPLE 10
Cultivation of fish (3)

To a 1 ton aquarium were charged the aqueous bivalent iron salt solution (iron content: $10^{-15}$ moles/liter) prepared in Preparation Example 1 and sea water. Thereafter, 50 crabs (25 kilograms) of the family Atelecyclidae were introduced and bred therein for 7 days. The total weight of the 50 crabs bred in this aquarium was 24 kilograms after 7 days, but that of those bred in an aquarium charged with an ordinary sea water was 15 kilograms after 7 days. Namely, the addition of the aqueous bivalent iron salt solution successfully prevented weight loss of the crabs.

EXAMPLE 11
Quality preservation of vegetable (1)

Spinach was immersed in the aqueous bivalent iron salt solution (iron content: $10^{-15}$ moles/liter) prepared in Preparation Example 1 for 10 minutes. After the solution was strained well from the spinach, the spinach was packed in a vinyl chloride bag and left to stand at 20° C. for 7 days. The thus treated spinach underwent no discoloration even after 7 days, but spinach immersed in an ordinary water turned completely black after 7 days.

EXAMPLE 12
Quality preservation of vegetable (2)

A zeolite was immersed in the aqueous bivalent iron salt solution (iron content: $10^{-15}$ moles/liter) prepared in Preparation Example 1 for 24 hours. The thus treated zeolite was applied to the inner surface of a vinyl chloride bag, and spinach was packed in the bag and left to stand at 20° C. for 7 days. The spinach packed in the thus treated vinyl chloride bag underwent no discoloration even after 7 days, but spinach preserved in an ordinary vinyl chloride bag turned completely black after 7 days.

The similar effect was exhibited, when slices of pork and tuna were treated in the same manner as described above.

EXAMPLE 13
Application to cosmetics (1)

To 50 grams of a hand cream was added 1 milliliter of the aqueous bivalent iron salt solution (iron content: $10^{-15}$ moles/liter) prepared in Preparation Example 1, and spreadability of the resulting cream on the skin, texture thereof, etc. were evaluated. The resulting hand cream showed notably improved spreadability. When the hand cream was continuously used once a day for one month, spots on the skin were moderated to such a degree as can be recognized visually.

EXAMPLE 14
Application to cosmetics (2)

To 100 milliliters of an ordinary hair dressing liquid was added 1 milliliter of the aqueous bivalent iron salt solution (iron content: $10^{-15}$ moles/liter) prepared in Preparation Example 1, and the resulting hair dressing liquid was sprayed over the hair as the finishing process of perming. When this hair dressing liquid was used for 3 months, the moisture of the hair was maintained in good condition with no damage of the hair. On the other hand, when an ordinary hair dressing liquid was used for three months, damage to the hair was observed.

EXAMPLE 15
Application to cosmetics (3)

To 100 grams of an ordinary skin lotion was added 1 milliliter of the aqueous bivalent iron salt solution (iron content: $10^{-15}$ moles/liter) prepared in Preparation Example 1. When this skin lotion was used, the moisture of the skin was improved and also urtication of the skin was moderated.

The similar effect was exhibited when the solution was added to an another lotion, a hair tonic or a skin oil. Particularly, the resulting hair tonic was successful in reducing dandruff and urtication.

EXAMPLE 16
Application to detergent

To 100 milliliters of a domestic neutral detergent was added 1 milliliter of the aqueous bivalent iron salt solution (iron content: $10^{-15}$ moles/liter) prepared in Preparation Example 1, and the resulting detergent was used by 20 monitors continuously for 3 months. The resulting detergent showed improved washing power over the non-incorporated detergent and caused no troubles of skin or fingers such as chapping, When the aqueous bivalent iron salt solution was applied to a shampoo, the similar effect was exhibited, and the use of the shampoo reduced dandruff and urtication.

EXAMPLE 17
Promotion of health

One hundred infants were selected at random, and 50 of them were allowed to drink the aqueous bivalent iron salt solution (iron content: $10^{-15}$ moles/liter) prepared in Preparation Example 1 continuously in an amount of 100 milliliters a day for three months. The percentage outbreak of colds during the winter of the year was investigated for the administered group and the nonadministered group, the percentage outbreak of cold in the administered group was 5%, while that in the nonadministered group was 25%.

EXAMPLE 18
Treatment of disease (1)

Zeolite was immersed in the aqueous iron salt solution (iron content: $10^{-15}$ is moles/liter) prepared in Preparation Example 1 for 24 hours. And the resulting zeolite was applied on the inner surface of a mask. When a patient of heavy asthma was allowed to wear the thus treated mask, the condition of asthma was treated in one week.

EXAMPLE 19
Treatment of disease (2)

When a patient of pollinosis (hay fever) was allowed to wear a mask immersed in the aqueous bivalent iron salt solution (iron content: $10^{-15}$ moles/liter) prepared in Preparation Example 1 for 24 hours and dried, the condition of snivelling disappeared immediately after wearing.

EXAMPLE 20
Treatment of disease (3)

When a patient of terminal breast carcinoma was administered with the aqueous bivalent iron salt solution (iron content: $10^{-15}$ moles/liter) prepared in Preparation Example 1 in an amount of 400 milliliters per day, the diameter of the carcinoma tissue was halved in 50 days, and the ascites and swelling were completely healed. Further, the carcinoma tissue was reduced to such a degree that it cannot be detected roentgenoscopically.

EXAMPLE 21
Treatment of disease (4)

When a patient of cirrhosis was administered with the aqueous bivalent iron salt solution (iron content: $10^{-15}$ moles/liter) prepared in Preparation Example 1 in an amount of 400 milliliters per day, GOT (Glutamate Oxalacetate Transaminase) value dropped from 120 to 55, and GPT (Glutamate Pyruvate Transaminase) value from 68 to 47 in a few days, and the subjective symptom was also greatly improved.

EXAMPLE 22
Treatment of disease (5)

When a patient having an intracerebral hematoma which is as big as a ping-pong ball was administered with the aqueous bivalent iron salt solution (iron content: $10^{-15}$ moles/liter) prepared in Preparation Example 1 in an amount of 400 milliliters per day, disappearance of the hematoma was identified in 50 days, and the subjective symptom was also greatly improved.

EXAMPLE 23
Treatment of disease (6)

To a 200 liter bath tub was introduced 200 grams of zeolite having been immersed in the aqueous bivalent iron salt solution (iron content: $10^{-15}$ moles/liter) prepared in Preparation Example 1 for 24 hours. When a patient of athlete's foot bathed in this bath repeatedly for 2 months, the symptom of athlete's foot was completely cured.

EXAMPLE 24
Treatment of disease (7)

NaCl was recrystallized from the aqueous bivalent iron salt solution (iron content: $10^{-15}$ moles/liter) prepared in Preparation Example 1, and 3 grams of the thus obtained NaCl was added to 100 grams of a tooth paste. When a patient of pyorrhea alveolaris was allowed to use this tooth paste for one month, the symptom of pyorrhea alveolaris was improved.

EXAMPLE 25
Promotion of growth of animal

Mice were bred by administering 20 milliliters of the aqueous bivalent iron salt solution (iron content: $10^{-15}$ moles/liter) prepared in Preparation Example 1. The mice bred with this aqueous solution showed 30% greater gain in the body weight after 10 days than mice bred with an ordinary water.

EXAMPLE 26
Deodorant action

When the aqueous bivalent iron salt solution (iron content: $10^{-15}$ moles/liter) prepared in Preparation Example 1 was sprayed in a dry fish producing plant filled with an offensive odor, the offensive odor was greatly reduced immediately after spraying.

EXAMPLE 27
Prevention of food perishing

Boiled fish paste was produced using the NaCl recrystallized from the aqueous bivalent iron salt solution (iron content: $10^{-15}$ moles/liter) prepared in Preparation Example 1. The fish paste produced using the NaCl did not perished after storage at 25° C. for 20 days, but the one produced using the ordinary NaCl perished after 7 days.

The similar effect was exhibited when the NaCl was used for the production of noodle (processed foodstuff made from wheat flour etc.).

EXAMPLE 28
Prevention of molding of wall

To 20 kilograms of an aqueous paint was added 200 milliliters of the aqueous bivalent iron salt solution (iron content: $10^{-15}$ moles/liter) prepared in Preparation Example 1, and the resulting mixture was applied onto the wall surface of a bath room. The wall surface did not get moldy even after 6 months, but the wall surface of a bath room coated with an ordinary aqueous paint got moldy after 2 months.

EXAMPLE 29
Prevention of metal corrosion

To 100 milliliters of the aqueous bivalent iron salt solution (iron content: $10^{-15}$ moles/liter) prepared in Preparation Example 1 was added 100 milligrams of hydroxylamine as an antioxidant. Iron pieces were immersed in the resulting mixture for 24 hours, and the thus treated iron pieces were immersed in a 1% aqueous saline solution to observe any change in their appearance thereafter. The thus treated iron piece underwent no corrosion even after 30 days, but untreated iron pieces underwent corrosion in 7 days.

The effect of the present solution can be exhibited by immersion for 1 to 30 hours.

EXAMPLE 30
Modification of water quality (1)

A ceramic material was immersed in the aqueous bivalent iron salt solution (iron content: $10^{-15}$ moles/liter) prepared in Preparation Example 1 for 24 hours to provide a filter medium. When a tap water (city water of Nagoya City, Japan) was filtered through the filter medium, irritating factors of taste and odor were removed from the tap water over one year or more, and the taste of the water became mild.

EXAMPLE 31

Modification of water quality (2)

A ceramic material was immersed in the aqueous bivalent iron salt solution (iron content: $10^{-15}$ moles/liter) prepared in Preparation Example 1 for 24 hours to provide a filter medium. The following tests were carried out using a water filtered through the filter medium (hereinafter referred to as a treated water) to obtain the following results.

(1) When the treated water was sprinkled over azalea trees for one month, notable rooting was observed and also the color of leaves was deepened.
(2) When 60 laying hens were allowed to take the treated water for one month, the egg-laying rate was improved by 5% and the also the offensive odor in the henhouse disappeared.
(3) When 5 milking cows were allowed to take the treated water for 3 months, the amount of milk collection was improved by 12%, and the cows no more suffered from mastitis.
(4) When the treated water was used as a bathing water, the condition of athlete's foot was moderated.
(5) When the treated water was used as a drinking water, conditions of hepatitis, pollinosis, constipation, cold, etc. were improved.
(6) When the treated water was used for culturing eels, the growing rate was triple in one month compared with those cultured using an ordinary water.
(7) When the treated water was sprayed in a room, the offensive odor of the room was removed.
(8) When noodles were prepared using the treated water, the noodles remained unperished over an extended time.
(9) When a soy sauce was produced using the treated water, the period of fermentation was reduced, and the taste of the soy sauce became milder.

EXAMPLE 32

Modification of air quality

A zeolite was impregnated with the aqueous bivalent iron salt solution (iron content: $10^{-15}$ moles/liter) prepared in Preparation Example 1 for 24 hours and dried. An air filter packed with the thus treated zeolite was prepared, and a plant (spinach) was cultured in the air filtered through this air filter. The thus cultured plant showed 50% weight gain (in terms of fresh weight) after one month compared with the plant cultured in the ordinary air. The effect of the present solution can be exhibited by immersion for 1 to 30 hours.

When the above air filter was attached to the air inlet of an automotive engine, the contents of hydrocarbon, nitrogen oxides, etc. in the exhaust gas were reduced.

EXAMPLE 33

Purification of waste water

When iron and copper pieces immersed in the aqueous bivalent iron salt solution (iron content: $10^{-15}$ moles/liter) prepared in Preparation Example 1 for 24 hours were introduced into the domestic discharge water, the turbidity of the waste water was reduced to notably increase the clarity of the water. The purification of the waste water was also identified numerically as shown in the following Table 1. The effect of the present solution can be exhibited by immersion for 1 to 30 hours.

TABLE 1

Data of domestic waste water treatment

|  | Before introduction of metal pieces | After introduction of metal pieces |
|---|---|---|
| BOD (*1) (Biological Oxygen Demand) | 6,200 | 5 |
| COD (*1) (Chemical Oxygen Demand) | 1,800 | 10 |
| SS (*1) (Suspended solid) | 83 | 7 |
| Content of the material extracted by normal hexane (*1) | 430 | 2.5 |
| E. Coli Count (*2) | $8 \times 10^6$ | $4 \times 10^2$ |

(*1): Unit = ppm
(*2): Unit = number/milliliter

EXAMPLE 34

Modification of oil quality

When 0.1 milliliter of the aqueous bivalent iron salt solution (iron content: $10^{-15}$ moles/liter) prepared in Preparation Example 1 was added to 1 liter of a light oil, the boiling point of the light oil was dropped by 2° C to improve combustibility thereof. On the other hand, when an ordinary water was added to a light oil, no drop in the boiling point was observed.

EXAMPLE 35

Improvement of fuel consumption

When 300 to 500 grams of iron and copper pieces immersed in the aqueous bivalent iron salt solution (iron content: $10^{-15}$ moles/liter) prepared in Preparation Example 1 for 24 hours were introduced to the gasoline tank of an automobile, it was identified that mileage per 1 liter of gasoline was improved by 23% and the effect lasted at least 6 months.

The effect of the present solution can be exhibited by immersion for 1 to 30 hours.

EXAMPLE 36

Purification of exhaust gas

The aqueous bivalent iron salt solution (iron content: $10^{-15}$ moles/liter) prepared in Preparation Example 1 was added to a gasoline in an amount of 1/10,000 per gasoline. When an automobile was allowed to run using the resulting gasoline, the exhaust gas was notably purified as shown in the following Table 2.

TABLE 2

Data of exhaust gas measurement

|  | Incorporated gasoline | Nonincorporated gasoline |
|---|---|---|
| Carbon monoxide | 7 ppm | 78 ppm |
| Hydrocarbon | 5 ppm | 19 ppm |
| Nitrogen oxides | 0.5 ppm | 6.2 ppm |

EXAMPLE 37

Prevention of electrification

When the aqueous bivalent iron salt solution (iron content: $10^{-15}$ moles/liter) prepared in Preparation Example 2 was applied to a vinyl chloride film, the frictional electrification voltage thereof notably dropped to 120 volts from the initial value before application of the solution of 5,000 volts.

EXAMPLE 38
Reduction of frictional resistance

When 1.0 milliliter of the aqueous bivalent iron salt solution (iron content: $10^{-15}$ moles/liter) prepared in Preparation Example 2 was added to 10 liters of a silicone lubricating oil, the frictional resistance of the lubricating oil was reduced by 30% over the nonincorporated oil.

EXAMPLE 39
Reinforcement of concrete

When 1 liter of the aqueous bivalent iron salt solution (iron content: $10^{-15}$ moles/liter) prepared in Preparation Example 2 was added to 1 liter of water to use the resulting solution for kneading a concrete, the thus kneaded concrete showed 50% improvement in the compression strength over the one kneaded with an ordinary water.

EXAMPLE 40
Melting of snow on the road surface (1)

The aqueous bivalent iron salt solution (iron content: $10^{-15}$ moles/liter) prepared in Preparation Example 2 was preliminarily sprinkled uniformly over the road surface in an amount of 1 liter per 1 $m^2$ to examine the thawing rate when snow fell. The amount of melted snow on the treated road surface was distinctly different as can visually be observed from that on the untreated road surface. Incidentally, the test was carried out on a windless fine day within the time period from 1 to 3 p.m., and the average temperature in this time period was 7° C.

EXAMPLE 41
Melting of snow on the road surface (2)

When 1 ton of asphalt was kneaded with 1 liter of the aqueous bivalent iron salt solution (iron content: $10^{-15}$ moles/liter) prepared in Preparation Example 2 and the thus kneaded asphalt was used for paving a road surface, the same thawing effect as in Example 40 was exhibited in contrast with the road surface having an ordinary asphalt pavement.

APPLICABILITY IN INDUSTRIES

As has been described above, the present bivalent iron compound, aqueous solution thereof and inorganic materials treated with such solutions can be utilized in various applications, for example, promotion of biological activities of seeds, modification of soil quality, quality preservation of vegetables, etc. in the field of agriculture; quality preservation of fishes, culturing of fishes, etc. in the field of fishing; promotion of health and treatment of diseases in the medical field; improvement of cosmetics or detergents, promotion of growth of animals, deodorizing, prevention of food perishing, prevention of molding on the walls, prevention of metal corrosion, modification of water, air, etc., purification of waste water and exhaust gas, modification of oils, prevention of electrification, reduction of frictional resistance, reinforcement of concrete, melting of snow on the road surface, etc.

The present bivalent iron compounds, aqueous solutions thereof and inorganic materials treated with such solutions can exhibit very excellent effects in each application over an extended period.

What is claimed is:

1. An aqueous solution comprising:
    (a) 1.0 mol of an iron compound;
    (b) 0.1 to 3.0 mol of a reducing material;
    (c) 0.1 to 3.0 mol of an amino acid; and
    (d) 1.0 liter of water to form the aqueous solution.

2. An aqueous solution in accordance with claim 1, wherein said iron compound is selected from the group consisting of iron dichloride, iron sulfate, iron dinitrate, iron diformate, iron diacetate, iron dipropionate, iron oxalate, iron tartrate, iron fumarate and iron dilactate.

3. An aqueous solution in accordance with claim 1, wherein said iron compound is the reaction product of a tervalent iron salt and a reducing material.

4. An aqueous solution in accordance with claim 3, wherein said tervalent iron salt is selected from the group consisting of iron trichloride, diiron trisulfate, iron trinitrate, iron phosphate, diiron diammonium tetrasulfate, iron triformate, iron triacetate, iron citrate and iron tristearate, and said reducing material is selected from the group consisting of formaldehyde, acetaldehyde, benzaldehyde, sucrose, glucose, lactose, formic acid, ascorbic acid, α-tocopherol, iron, zinc and copper.

5. An aqueous solution in accordance with claim 1, wherein said reducing material is selected from the group consisting of formaldehyde, acetaldehyde, benzaldehyde, sucrose, glucose, lactose, formic acid, ascorbic acid, α-tocopherol, iron, zinc and copper.

6. An aqueous solution in accordance with claim 1, wherein said amino acid is selected from the group consisting of glycine, alanine, leucine, tyrosine, threonine, serine, proline, tryptophan, methionine, cystine, cysteine, asparagic acid, glutamic acid, lysine, arginine and histidine.

7. A composition comprising an aqueous solution, said aqueous solution comprising:
    (a) 1.0 mol of an iron compound;
    (b) 0.1 to 3.0 mol of a reducing material;
    (c) 0.1 to 3.0 mol of an amino acid; and
    (d) 1.0 liter of water to form the aqueous solution, said aqueous solution is diluted to have an iron concentration from about $1\times10^{-6}$ to about $1\times10^{-21}$ moles per liter, and wherein the composition is selected from the group consisting of a skin lotion, a skin oil, a hair tonic, a shampoo and a detergent, wherein said aqueous solution is present in an effective amount to improve said composition.

8. A composition in accordance with claim 7, wherein said compound is selected from the group consisting of iron dichloride, iron sulfate, iron dinitrate, iron diformate, iron diacetate, iron dipropionate, iron oxalate, iron tartrate, iron fumarate and iron dilactate.

9. A composition in accordance with claim 7, wherein said iron compound is the reaction product of a tervalent iron salt and a reducing material.

10. A composition in accordance with claim 1, wherein said tervalent iron salt is selected from the group consisting of iron trichloride, diiron trisulfate, iron trinitrate, iron phosphate, diiron diammonium tetrasulfate, iron triformate, iron triacetate, iron citrate and iron tristearate, and said reducing material is selected from the group consisting of formaldehyde, acetaldehyde, benzaldehyde, sucrose, glucose, lactose, formic acid, ascorbic acid, α-tocopherol, iron, zinc and copper.

11. A composition in accordance with claim 7, wherein said reducing material is selected from the group consisting of formaldehyde, acetaldehyde, benzaldehyde, sucrose, glucose, lactose, formic acid, ascorbic acid, α-tocopherol, iron, zinc and copper.

12. A composition in accordance with claim 7, wherein said amino acid is selected from the group consisting of glycine, alanine, leucine, tyrosine, threonine, serine, proline, tryptophan, methionine, cystine, cysteine, asparagic acid, glutamic acid, lysine, arginine and histidine.

13. A method for treating an inorganic material comprising the steps of:
(i) immersing said inorganic material in an aqueous solution, the aqueous solution comprising:
(a) 1.0 mol of an iron compound;
(b) 0.1 to 3.0 mol of a reducing material;
(c) 0.1 to 3.0 mol of an amino acid; and
(d) 1.0 liter of water;
(ii) removing said inorganic material from the aqueous solution,
wherein from about 0.1 to about 3.0 moles of reducing material and from about 0.1 to about 3.0 moles of amino acid are added to about 1.0 mol of bivalent iron compound and about 1.0 liter of water to form the aqueous solution, and
wherein when said aqueous solution is used, said aqueous solution is diluted to have an iron concentration from abut $1 \times 10^{-6}$ to about $1 \times 10^{-21}$ moles per liter.

14. A method for treating an inorganic material in accordance with claim 13, wherein said inorganic material is selected from the group consisting of iron, zinc, copper, a ceramic or inorganic salt.

15. A method for treating an inorganic material in accordance with claim 14, wherein said ceramic is selected from the group consisting of a zeolite, silicon carbide, alumina, silicon nitride or cordierite.

16. A method for treating an inorganic material in accordance with claim 13, wherein said iron compound is selected from the group consisting of iron dichloride, iron sulfate, iron dinitrate, iron diformate, iron diacetate, iron dipropionate, iron oxalate, iron tartrate, iron fumarate and iron dilactate.

17. A method for treating an inorganic material in accordance with claim 13, wherein said iron compound is the reaction product of a tervalent iron salt and a reducing material.

18. A method for treating an inorganic material in accordance with claim 17, wherein said tervalent iron salt is selected from the group consisting of iron trichloride, diiron trisulfate, iron trinitrate, iron phosphate, diiron diammonium tetrasulfate, iron triformate, iron triacetate, iron citrate and iron tristearate, and said reducing material is selected from the group consisting of formaldehyde, acetaldehyde, benzaldehyde, sucrose, glucose, lactose, formic acid, ascorbic acid, α-tocopherol, iron, zinc and copper.

19. A method for treating an inorganic material in accordance with claim 13, wherein said reducing material is selected from the group consisting of formaldehyde, acetaldehyde, benzaldehyde, sucrose, glucose, lactose, formic acid, ascorbic acid, α-tocopherol, iron, zinc and copper.

20. A method for treating an inorganic material in accordance with claim 13, wherein said amino acid is selected from the group consisting of glycine, alanine, leucine, tyrosine, threonine, serine, proline, tryptophan, methionine, cystine, cysteine, asparagic acid, glutamic acid, lysine, arginine and histidine.

21. A method for treating an inorganic material in accordance with claim 13, wherein said method further comprises the step of immersing the inorganic material in water after removing the inorganic material from the aqueous solution.

22. The treated inorganic material produced by the method of claim 13.

* * * * *

UNITED STATES PATENT AND TRADEMARK OFFICE
CERTIFICATE OF CORRECTION

PATENT NO. : 6,306,201 B1
DATED : October 23, 2001
INVENTOR(S) : Shinzi Makino

It is certified that error appears in the above-identified patent and that said Letters Patent is hereby corrected as shown below:

<u>Title page,</u>
Delete the title in its entirety and replace it with -- AN A AQUEOUS SOLUTION COMPRISING AN IRON COMPOUND, AN AMINO ACID AND A REDUCING AGENT --.

<u>Column 1,</u>
Line 1, delete the title in its entirety and replace it with -- AN A AQUEOUS SOLUTION COMPRISING AN IRON COMPOUND, AN AMINO ACID AND A REDUCING AGENT --.
Lines 10-11, delete "Nov. 24, 1988." and replace it with -- May 22, 1990. --

<u>Column 2,</u>
Line 21, delete "$FeC_2$" and replace it with -- $FeCl_2$ --.
Line 24, delete "(Fe(CHCOO) )" and replace it with -- $(Fe(CH_3COO)_2)$ --.

<u>Column 8,</u>
Line 27, delete "perished" and replace it with -- perish --.

<u>Column 9,</u>
Line 16, delete "and the also" and replace it with -- and also --.

<u>Column 13,</u>
Line 19, delete "abut" and replace it with -- about --.

Signed and Sealed this

Second Day of July, 2002

*Attest:*

JAMES E. ROGAN
*Attesting Officer*  *Director of the United States Patent and Trademark Office*

UNITED STATES PATENT AND TRADEMARK OFFICE
CERTIFICATE OF CORRECTION

PATENT NO.    : 6,306,201 B1
DATED         : October 23, 2001
INVENTOR(S)   : Shinzi Makino It is certified that error appears in the above-identified patent and that said Letters Patent is hereby corrected as shown below:

<u>Title page,</u>
Item [54], delete the title in its entirety and replace it with -- AN AQUEOUS SOLUTION COMPRISING AN IRON COMPOUND, AN AMINO ACID AND A REDUCING AGENT --.

<u>Column 1,</u>
Line 1, delete the title in its entirety and replace it with -- AN AQUEOUS SOLUTION COMPRISING AN IRON COMPOUND, AN AMINO ACID AND A REDUCING AGENT --.
Lines 10-11, delete "Nov. 24, 1988." and replace it with -- May 22, 1990. --

<u>Column 2,</u>
Line 21, delete "$FeC_2$" and replace it with -- $FeCl_2$ --.
Line 24, delete "(Fe(CHCOO) )" and replace it with -- $(Fe(CH_3COO)_2)$ --.

<u>Column 8,</u>
Line 27, delete "perished" and replace it with -- perish --.

<u>Column 9,</u>
Line 16, delete "and the also" and replace it with -- and also --.

<u>Column 13,</u>
Line 19, delete "abut" and replace it with -- about --.

This certificate supersedes Certificate of Correction issued July 2, 2002.

Signed and Sealed this

Eighth Day of October, 2002

*Attest:*

JAMES E. ROGAN
*Attesting Officer*     *Director of the United States Patent and Trademark Office*